United States Patent [19]

Holtkamp, Sr.

[11] Patent Number: Plant 6,848

[45] Date of Patent: Jun. 13, 1989

[54] AFRICAN VIOLET PLANT NAMED DALLAS

[76] Inventor: Reinhold Holtkamp, Sr., Werther Strasse 112, D4294 Isselburg, Fed. Rep. of Germany

[21] Appl. No.: 152,845

[22] Filed: Feb. 5, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Dallas characterized by its single, purplish pink flowers with wavy edges and darker pink center; strong, upright flower stems that curve toward the center to form a bouquet above the leaves; bright green, serrated girl-type leaves; profuse flowering, vigorous and compact growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Dallas.

The new cultivar was referred to during the breeding and selection process by the designation G 30/6, and is a product of a planned breeding program. The new cultivar was originated from a cross made by me in the controlled breeding program in Isselburg, Federal Republic of Germany. The female, or seed parent was a cultivar designated 349/0. The male, or pollen parent was a cultivar designated 4158.

Dallas was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Dallas has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Dallas, which in combination distinguish this African violet as a new and distinct cultivar:

(1) Strong, upright flower stems curving slightly toward the center.

(2) Purplish pink single flowers with darker center and wavy edges.

(3) Profuse flowering.

(4) Each plant carries 8–9 and more upright flower stems each of which carries 5–7 and more flowers.

(5) Long lasting, non-dropping flowers.

(6) Vigorous and compact grower.

(7) Plant saleable 10 to 11 weeks after potting.

(8) Seeds capsules push slightly through.

(9) Bright green girl-type leaves, wavy, serrated and having a bright light green center.

(10) After maturity the flowers dry off, and remain on the peduncle without becoming infected by botrytis.

The accompanying color photographic drawing shows a typical specimen plant of the new culture. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 2 p.m. in Nashville, Tenn.

Botanical classification: *Saintpaulia ionantha,* Ramt., c.v. Dallas.

Parentage:

*Male parent.*—4158.

*Female parent.*—349/0.

Propagation: The new cultivar holds its distinguishing characteristics through successive propagations by leaf cuttings.

Plant: From 9 cm to 12 cm tall when grown in pots, and approximately 18–21 cm in diameter when fully grown.

*Leaves.*—General form: Round, girl-type. Diameter: 65–75 mm. Texture: Leather-like. Aspect: Serrated, wavy, shiny, hairy, bright light green center. Veins: Upperside: well visible; Underside: well pronounced, light green, shiny. Color (upperside): Yellow-Green Group 147 between A and B. Color (underside): Greyed-Green Group 193 B. Petiole: Strong upright, light green with purplish touch, hairy.

*Flowers.*—Buds: Bell-shaped, 8–9 mm just before opening, light pink. Sepals: Five (5). Color: Brownish green. Calyx: Shape: Funnel-shaped. Aspect: Spear-shaped, hairy. Peduncle: Character: Strong upright, hairy. Color: Purplish green. Individual flowers: Size: 40–45 mm. Shape: Single violet-shaped (3 large and 2 small petals), wavy edges. Color (upperside): Purple Group 75 between A and B. Under cooler temperatures and more intensive lighting, the purplish pink tends to intensify. Color (underside): Purple Group 78 between B and C. Borne: Each flower stem carries 5–7 and more flowers on strong, upright peduncle that are free standing above the leaves, thereby forming a compact bouquet. Flowering habit: Flowers 10–11 weeks after potting.

*Reproductive organs.*—Stamens: 2. Anthers: 2 composed of 4 anther cells, seed capsule pushes slightly through. Filaments: Yellowish green with pink traces 5 mm long. Pollen color: Yellow Group 7 A. Styles: 7–8 mm long, purplish pink, base of ovary light green and hairy.

*Roots.*—Normally developed, white when young, turning slightly brownish when older.

Disease resistance: Good.

General observations: Dallas has a very attractive appearance due to its bright green, serrated girl-type leaves with a light green center. A tight bouquet of flowers free standing above the leaves develops after approximately 10–11 weeks. Each of the 8–9 and more flowers stems carries 5–7 and more purplish pink, single, violet-shaped flowers with wavy edges.

The purplish pink color in the center of the flower is darker and radiates somewhat into the two smaller petals. Occasionally, 1–2 additional small petals may develop. The flowers are long-lasting and non-dropping and the seed capsules may develop. The flowers are long-lasting and non-dropping and the seed capsules push slightly through.

I claim:

1. A new and distinct cultivar of African violet named Dallas, as described and illustrated, and particularly characterized by its single, purplish pink flowers with wavy edges and darker pink center; strong, upright flower stems that curve toward the center to form a bouquet above the leaves; bright green, serrated girl-type leaves; profuse flowering, vigorous and compact growth habit, flowering 10–11 weeks after potting, and its long-lasting and non-dropping flowers.

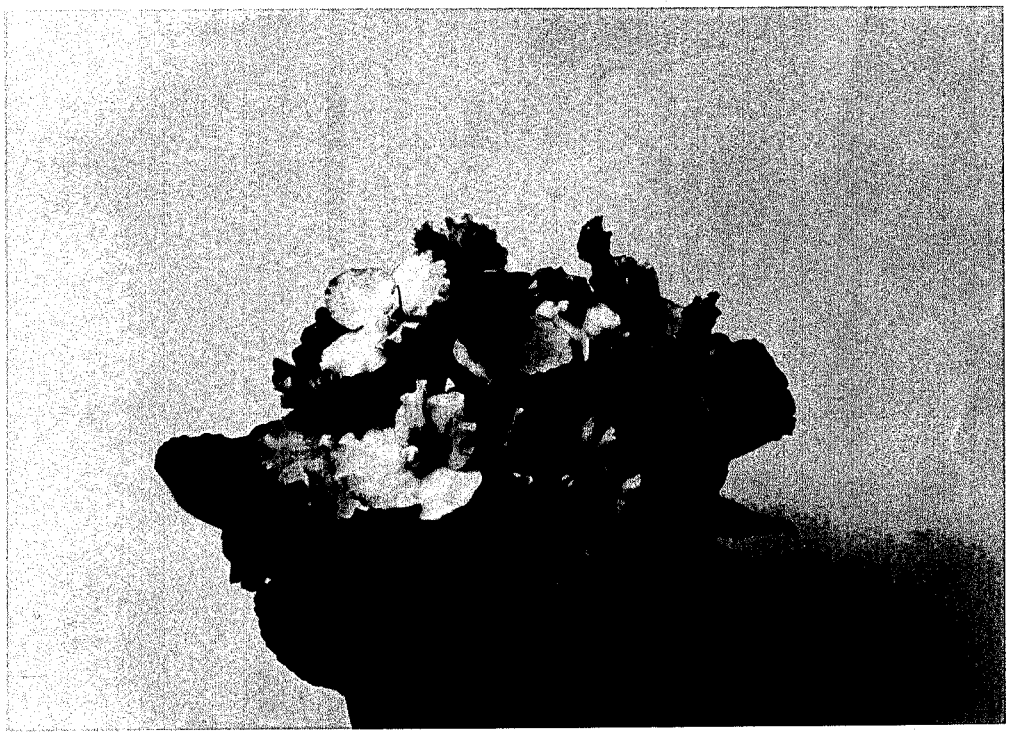

* * * * *